United States Patent [19]

Johnson

[11] Patent Number: 4,971,761
[45] Date of Patent: Nov. 20, 1990

[54] TEMPERATURE CONTROL METHOD FOR AN ETHYLENE OXIDE STERILIZATION CYCLE

[75] Inventor: Kenneth A. Johnson, Walworth, N.Y.

[73] Assignee: MDT Corporation, Torrance, Calif.

[21] Appl. No.: 319,049

[22] Filed: Mar. 6, 1989

[51] Int. Cl.$^5$ .......................... A61L 2/20; A61L 2/24
[52] U.S. Cl. ........................ 422/34; 422/28; 422/109; 422/242; 422/295
[58] Field of Search ............ 422/26, 27, 28, 34, 422/109, 111, 112, 242, 292, 295

[56] References Cited

U.S. PATENT DOCUMENTS 4,284,600 8/1981 Gillis et al. ................ 422/109 X

OTHER PUBLICATIONS

"American National Standard ST 24", a brochure by the Association for the Advancement of Medical Instrumentation, cover sheet and p. 4, ANSI/AAMI-1987.
"Ethylene Oxide Processing with Castle Equipment", pp. 2-3 through 2-6, product literature, The Castle Company, Henrietta, New York.

Primary Examiner—Robert J. Warden
Assistant Examiner—Jill Johnston
Attorney, Agent, or Firm—Trask, Britt & Rossa

[57] ABSTRACT

Cooling water is circulated through the heating water jacket of a gas sterilizer during the initial gas pressurization phase to reduce the temperature rise within the sterilization chamber caused by the heat of compression of the gas.

19 Claims, 1 Drawing Sheet

TEMPERATURE CONTROL METHOD FOR AN ETHYLENE OXIDE STERILIZATION CYCLE

BACKGROUND OF THE INVENTION

1. Field:

This invention relates to chemical gas sterilization. It is particularly directed to ethylene oxide sterilization and provides an improved method for controlling temperatures within a sterilization chamber at the initial stage of the cycle.

2. State of the Art:

Chemical sterilization using biocidal gases, notably ethylene oxide, is a well-established procedure in various fields of applied biological science, particularly in the health care professions. Standards have evolved for such procedures and have been published as American National Standard ST24 by the Association for the Advancement of Medical Instrumentation (AAMI) (ANSI/AAMI ST24-1987). Standard ST24 sets forth certain physical performance tests, including the following:

... 3.1.5.6 "Physical Performance Tests." (1) Temperature Control. After exposure pressure has been reached and exposure timing has begun, the chamber temperature shall stabilize within the first ten percent of the selected exposure time, after which the variation of temperature within the chamber may not exceed ±3° C. (5.5° F.) throughout the remaining exposure phase of the cycle....

Ethylene oxide (EO) sterilization is often conducted in a water-jacketed pressure chamber. The sterilization process is initiated by evacuating the chamber to remove air. Moisture is introduced during a conditioning phase. The EO sterilant is then introduced to the chamber to a predetermined pressure, usually above atmospheric. As suggested by the physical performance test of Standard ST24, one of the most important process parameters for EO sterilization is temperature control. Typically, temperatures are controlled by introducing steam to a water-filled jacket surrounding the sterilization chamber to balance heat losses through the unjacketed ends of the chamber. The steam causes the temperature of the jacket, and thus the chamber, to rise. When a predetermined jacket temperature is reached, steam is no longer introduced to the jacket. In time, the jacket temperature tends to drop as heat is dissipated to the ambient environment. Additional steam is introduced intermittently to maintain the temperature within the chamber at the setpoint (or within the prescribed tolerance band above the setpoint).

While use of the water jacket and steam provides good temperature control within the standards set by ANSI/AAMI ST24-1987, that test is performed using an empty chamber and ignores the impact on a load experiencing the actual temperature and pressure conditions within the chamber during the first ten percent (10%) of the time elapsing after the exposure pressure has been reached and exposure timing has commenced. Many of the plastics and delicate electronics in current use rely upon ethylene oxide sterilization procedures because they cannot withstand alternative methods of sterilization. Such modern loads are relatively intolerant to high temperatures. Accordingly, it is of significant importance to ensure that these delicate instruments and implements be protected from extreme temperatures throughout their entire exposure and not only during the last ninety percent (90%) of the exposure period.

Inherent in the EO sterilization procedures currently practiced, is an uncontrolled temperature surge at the commencement of the sterilization cycle. When EO sterilant is compressed within the chamber to a predetermined pressure (the gas pressurization phase), significant heat of compression is released within the chamber. This heat of compression typically causes the chamber temperature to rise briefly, e.g., by as much as 12° C. above the desired chamber temperature setpoint. The setpoint temperature is established within the chamber by heating the water jacket external of the chamber. Jacket heating is independent of the impact of any incidental heat of compression. Moreover, the aforementioned performance test is conducted at a time when the impact of the heat of compression is largely dissipated. Accordingly, under normal monitoring and test procedures, any impact of the heat of compression is ignored. Nevertheless, this impact is detrimental to the load subjected to the sterilization procedure.

Reliance upon ambient conditions to dissipate the heat of compression occurring in the gas pressurization phase of the sterilization procedure is inadequate. There remains a need in the art for an improved method whereby this heat of compression may be controlled sufficiently to safeguard delicate materials and instruments exposed to gas sterilization techniques.

SUMMARY OF THE INVENTION

According to the present invention, process expedients are followed to extract heat through the sidewalls of a gas sterilization chamber during the gas pressurization phase, thereby to anticipate and compensate for the heat of compression of the gas sterilant.

Because the sterilization chamber is ordinarily provided with a water jacket for introducing heat to the chamber at later stages of the cycle, it is convenient to utilize that jacket for the circulation of cooling fluid (typically water). By reducing the temperature of the jacket during the gas pressurization phase, heat is extracted from the chamber into the jacket, thereby reducing the excess heat in contact with a load at the commencement of an exposure phase.

At the commencement of the gas pressurization phase, cold water is allowed to enter and circulate within the jacket at an appropriate circulation rate and for a time period which may either be fixed or responsive to monitored conditions within the chamber. Ordinarily, cold water circulation is terminated no later than the commencement of the exposure phase. As a consequence of this cooling procedure, the peak temperature rise within the chamber is reduced, the setpoint (target) temperature is reached earlier in the cycle and the opportunity for a load to be temperature-damaged is reduced.

BRIEF DESCRIPTION OF THE DRAWINGS

In the drawing, which illustrates what is currently regarded as the best mode for carrying out the invention.

DESCRIPTION OF THE ILLUSTRATED EMBODIMENTS

Figure 1:
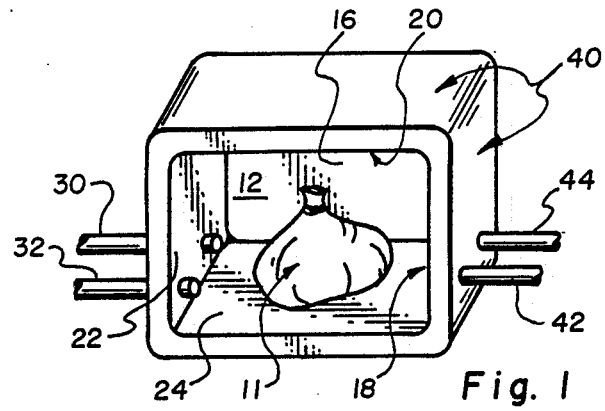
FIG. 1 is a schematic illustration of a water jacketed sterilizer chamber useful for the practice of this invention.
Figure 2:
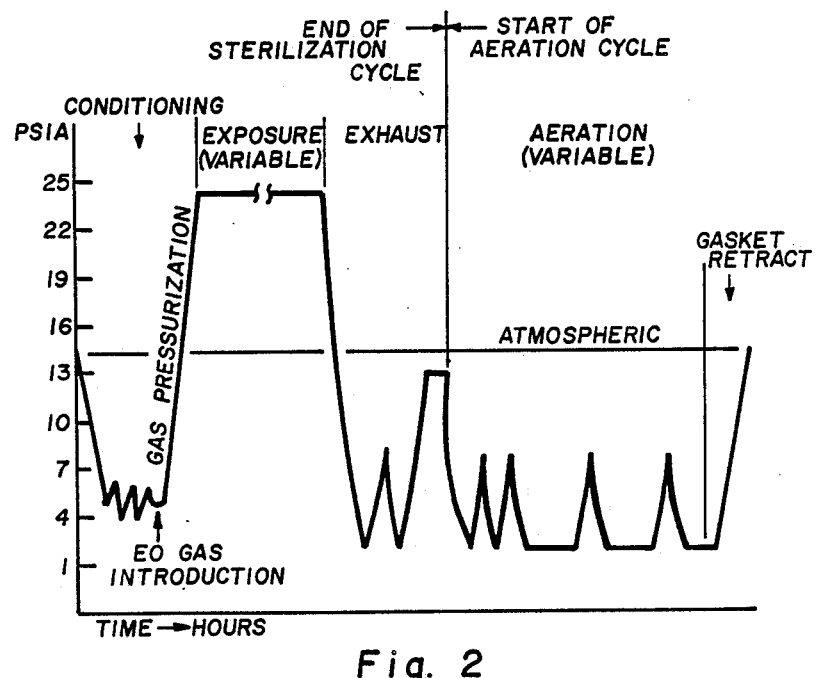
FIG. 2 is a graph diagram descriptive of a typical gas sterilization cycle pertinent to this invention.

Referring to FIGS. 1 and 2, a typical gas sterilization cycle involves placing a load 11, (illustrated as a textile pouch containing, for example, heat labile instruments), in sterilization chamber 12. The chamber 12 is defined by opposed endwalls, e.g. 16, connected by continuous sidewalls 18, 20, 22, 24. One of the endwalls is removed in FIG. 1 for clarity. This wall would normally comprise a sealable door. With the load in place, the door (not shown) is closed and a deep vacuum, e.g. below about 4 psia, is drawn, e.g. through the port 30, and held to remove substantially all of the air from the chamber 12. As shown by FIG. 2, the vacuum pressure may be pulsed during an initial conditioning period to facilitate air removal from the load 11. The pulses correspond to the introduction of humidity during this period. At the end of the conditioning period, EO gas (or other gas sterilant) is introduced, e.g. through the port 32. In a relatively short period, typically less than about 10 minutes, and as short as ½ minute, depending upon the chamber volume, sufficient gas is introduced to effect a preselected "target" or "exposure" pressure.

For a typical EO sterilization procedure utilizing a 1288 sterilant (twelve percent EO gas and 88 percent dichlorodifluoromethane), conventional practice involves the introduction of about 650 to about 750 milligrams (mg) of EO per liter (l) of chamber volume, which effects an exposure pressure in the range of about 8 to about 10 psig at the sterilization exposure temperatures normally employed (above ambient and below about 60° C.). Humidity within the chamber should normally exceed thirty percent (30%). A 1090 sterilant (ten percent EO gas and 90 percent $CO_2$) under similar circumstances would effect an exposure pressure on the order of about 25 psig.

Exposure times are measured from the time that the exposure pressure is reached within the chamber 12. The lower the temperature within the chamber, the longer the exposure time required to accomplish EO sterilization. A minimum of two hours is recommended at an exposure temperature of 55° C.; at least five (5) hours exposure is recommended at 38° C. Rarely would adequate EO sterilization be effected with an exposure time of less than an hour, even at 60° C. As illustrated, the sidewalls 18, 20, 22, 24 of the chamber 12 are surrounded by a water jacket 40. Heated water is circulated through the jacket 40; e.g., by means of pipes 42, 44 to establish and maintain a stable selected exposure temperature. In a typical procedure, steam is intermittently injected into the circulating water as needed to maintain the chamber and its contents at a temperature within the range between the setpoint temperature and about 2° C. above that temperature for the last ninety percent (90%) of the exposure period. Steam injection compensates for heat losses occurring through the endwalls, e.g., 16, and through the jacket 40 to the surrounding ambient environment.

Heating of the water being circulated just prior to and during gas pressurization is normally avoided because it would reinforce the undesirable impact of the heat of compression experienced during the gas pressurization phase of the cycle.

EXAMPLE

A typical EO sterilizer with an internal volume of about 255 liters utilizes a gas pressurization phase of about two minutes duration to avoid an unacceptably rapid release of the heat of compression of the EO introduced to the sterilization chamber.

Figure 3:
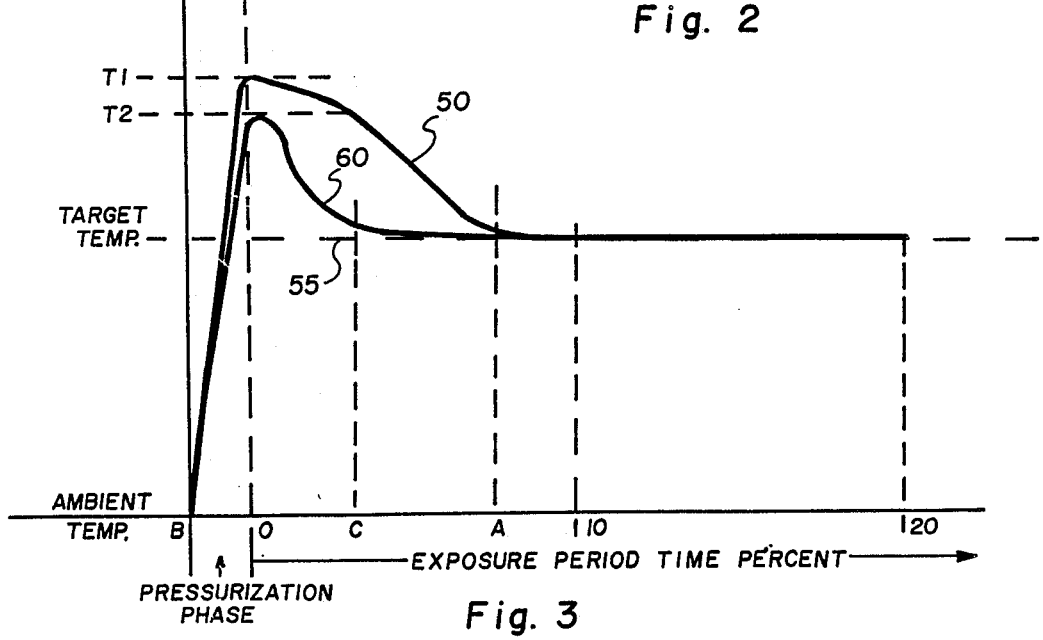
FIG. 3 is a graph diagram with theoretical curves illustrative of the invention.

Line 50 of FIG. 3 represents a temperature curve typical of an EO sterilization procedure of the type described with reference to FIGS. 1 and 2. Heating of the circulating water is not commenced until the temperature in the chamber approaches the target temperature, e.g., at elapsed time A. Prior to this time A, however, the temperature within the chamber 12 in contact with the load is substantially higher than the target temperature. The temperature T1 at the beginning of the exposure period may exceed the target temperature by 10° C. or more. The excess heat illustrated by the area bounded by the curve 50 and the target temperature line 55 represents a very significant hazard to delicate heat labile instruments.

Line 60 represents a typical temperature curve resulting from the modified procedure of this invention whereby cold water, about 20° C., is introduced to and circulated within the water jacket 40 commencing at time B, and continuing for approximately one minute during the EO pressurization phase of the cycle. Heating of the circulating water will ordinarily be commenced when the temperature reflected by curve 60 decreases to within about 2° C. from the temperature reflected by line 55. In this instance, the temperature overshoot beyond the target temperature is reduced, T2 typically being several degrees lower than T1. Of even greater practical significance, however, the curve 60 approaches the line 55 at a much earlier time C, and the excess heat (represented by the area under curve 60 and above line 55) imposed upon the load 11 by virtue of the heat of compression of EO is very significantly reduced. Moreover, the target exposure temperature is maintained over a larger percentage of the exposure time as compared to conventional practice.

FIG. 2 illustrates a conventional exhaust phase and aeration cycle typical of gas sterilization procedures. The present invention need not impact on those subsequent steps, being directed to an improvement which impacts primarily on the gas pressurization and exposure phases of a sterilization cycle.

Circulation of cold water throughout a greater portion of the EO pressurization phase would be expected to produce even better results than those illustrated by FIG. 3. Care should be taken to avoid overcooling, however. It is preferred that the temperature within the chamber 12 not be permitted to decrease to below the target temperature at any time during the exposure period.

Reference herein to details of the illustrated embodiments is not intended to limit the scope of the appended claims. The invention contemplates the adjustment of temperatures, circulation rates and other parameters to achieve a preferred temperature curve for a sterilization cycle, for example. In practice, cooling water temperatures between 0° C. and ambient temperature are operable, with temperatures below about 25° C., e.g. between about 10° and about 20° C. being preferred. The desired circulation time of cooling water varies with its initial temperature, its circulation rate, and the volume of the chamber. Unrefrigerated water is normally available at about 7° to about 20° C. Practical circulation rates, utilizing currently available pumps, typically range from about 0.04 to about 0.15 liters per minute per liter of chamber volume. Under those conditions, cold water circulation times of about ½ to about 5 minutes are considered to constitute the practical range for realizing the benefits of this invention.

What is claimed is:

1. In a gas sterilization procedure including the steps of placing a load to be sterilized within a chamber defined by opposing endwalls connected by sidewalls, one said endwall comprising a sealable entry into the interior of said chamber, evacuating said chamber to remove air, introducing sterilant gas into said evacuated chamber and compressing said sterilant gas to effect a predetermined exposure pressure within said chamber, and exposing said load to said sterilant gas within said chamber for an exposure period at said preselected exposure pressure while establishing and maintaining a temperature in said chamber within a preselected range by applying heat as needed through said sidewalls while permitting heat to escape through said endwalls, the improvement which comprises:

extracting heat through externally cooling said sidewalls during the period in which said gas is being compressed in said chamber, thereby to reduce the time interval during which the load is exposed to a temperature in excess of said preselected range by reason of the heat of compression of said sterilant gas.

2. The improvement according to claim 1, wherein the sidewalls of said chamber are provided in contact with a water jacket, heat is introduced to said chamber through said sidewalls by circulating hot water through said water jacket and heat is extracted from said chamber by circulating cold water through said water jacket.

3. An improvement according to claim 2, wherein said sterilant gas comprises ethylene oxide (EO).

4. The improvement according to claim 3, wherein heat is intermittently introduced as needed to establish a stabilized temperature within the first ten percent (10%) of said exposure period and heat is thereafter intermittently introduced throughout the remainder of the exposure period as needed to maintain the temperature in said chamber within a range of about 2° C. above said stabilized temperature.

5. The improvement according to claim 4, wherein cold water is circulated through said water jacket during the period in which EO is introduced into said chamber but not after said exposure pressure is achieved within said chamber.

6. The improvement according to claim 3, wherein the temperature within said chamber is stabilized within the first ten percent (10%) of said exposure period to a temperature above ambient but below about 60° C. and cold water is circulated through said water jacket for a period of time not exceeding the interval during which EO is introduced to said chamber.

7. The improvement according to claim 6, wherein the temperature of the cold water introduced to said water jacket is below ambient.

8. The improvement according to claim 7, wherein said cold water is introduced to said water jacket at a temperature below about 25° C. at a circulation rate of between about 0.04 and about 0.15 liters per minute per liter of chamber volume.

9. The improvement according to claim 8, wherein said cold water is introduced for a period of time between about ½ and about 5 minutes.

10. The improvement according to claim 9, wherein heating of the circulating water in said water jacket is commenced when the temperature within the chamber decreases from a peak level at the commencement of said exposure period to a level within about 2° C. from said stabilized temperature.

11. The improvement according to claim 9, wherein cold water is introduced for a period of less than about 1 minute.

12. The improvement according to claim 6, wherein said exposure period is of at least one hour's duration.

13. The improvement according to claim 12, wherein said exposure temperature is below about 55° C..

14. The improvement according to claim 13, wherein said exposure period is of at least 2 hours' duration.

15. The improvement according to claim 14, wherein the temperature of the cold water introduced to said water jacket is below ambient.

16. The improvement according to claim 15, wherein said cold water is introduced to said water jacket at a temperature below about 25° C. at a circulation rate of between about 0.04 and about 0.15 liters per minute per liter of chamber volume.

17. The improvement according to claim 16, wherein said cold water is introduced for a period of time between about ½ and about 5 minutes.

18. The improvement according to claim 17, wherein heating of the circulating water in said water jacket is commenced when the temperature within the chamber decreases from a peak level at the commencement of said exposure period to a level within about 2° C. from said stabilized temperature.

19. The improvement according to claim 18, wherein cold water is introduced for a period of less than about 1 minute.

* * * * *